United States Patent [19]

Turner et al.

[11] Patent Number: 4,976,772

[45] Date of Patent: Dec. 11, 1990

[54] 4-((ARYLOXY)PHENOXY)ALKENOL AS INTERMEDIATES AND HERBICIDES

[75] Inventors: James A. Turner, Pittsburg; Wendy S. Jacks, Walnut Creek, both of Calif.; Paul S. Zorner, Durham, N.C.

[73] Assignee: The Dow Chemical Company, Midland, Mich.

[21] Appl. No.: 435,095

[22] Filed: Nov. 13, 1989

Related U.S. Application Data

[62] Division of Ser. No. 901,844, Aug. 29, 1986, Pat. No. 4,900,354.

[51] Int. Cl.$^5$ .................... C07D 241/44; A01N 43/60
[52] U.S. Cl. .......................................... 71/92; 71/94; 544/354; 546/157
[58] Field of Search ............................ 544/354; 71/92

[56] References Cited

U.S. PATENT DOCUMENTS

| | | | |
|---|---|---|---|
| 4,525,205 | 6/1985 | Lee | 544/354 |
| 4,609,396 | 9/1986 | Fawzi | 71/92 |
| 4,629,493 | 12/1986 | Ura et al. | 71/94 |
| 4,661,149 | 4/1987 | Raju | 71/94 |
| 4,731,108 | 3/1988 | Turner et al. | 544/354 |
| 4,900,354 | 2/1990 | Turner et al. | 544/354 |

FOREIGN PATENT DOCUMENTS 8143269  4/1981  Japan .

OTHER PUBLICATIONS

Chemical Abstracts, vol. 95, 115318p (1981) for Japan Patent 81/43,269 (4/21/81).

*Primary Examiner*—Mukund J. Shah
*Assistant Examiner*—E. Bernhardt
*Attorney, Agent, or Firm*—S. Preston Jones; Ronald G. Brookens

[57] ABSTRACT 4-((Aryloxy)phenoxy)alkenols, their preparation and use as active herbicides for the postemergent control of grassy weeds. The compounds also are useful as intermediates for the preparation of herbicidal derivatives, which compounds are especially useful for the control of grassy weeds in the presence of corn plants.

33 Claims, No Drawings

4-((ARYLOXY)PHENOXY)ALKENOL AS INTERMEDIATES AND HERBICIDES

CROSS-REFERENCE TO RELATED APPLICATION

This is a divisional of application Ser. No. 901,844, filed Aug. 29, 1986, now U.S. Pat. No. 4,900,354.

BACKGROUND OF THE INVENTION

Highly active herbicidal compounds of the class constituting aryloxyphenoxyalkanoic, and aryloxyphenoxy. alkenoic acids and related compounds have been described in the patent literature. These compounds have been prepared by making derivatives of the acid function thereof and bearing various groups or substituents on, primarily, the aryl structure. Such compounds in which the aryloxy and O-alkanoic acid functions respectively are disposed in 1,4 relation on the phenyl group, are especially active against grassy, i.e., gramineous weeds while displaying little or no herbicidal activity against broadleaf plants and, often, only slight activity against cereal grains. However, these compounds as a group are generally injurious to corn, i.e., maize, and are of little use for controlling grassy weeds in corn crops.

SUMMARY OF THE INVENTION

The present invention relates to novel 4-((aryloxy)-phenoxy)alkenols which are useful as intermediates for preparing highly active herbicidal compounds, which compounds are particularly effective in selectively controlling grassy weeds in the presence of corn plants In addition, these compounds are active herbicides in their own right and are useful in controlling grassy weeds and especially controlling grassy weeds in the presence of many broadleaf crop plants.

The aryloxyphenoxyalkenols of the present invention correspond to the formula

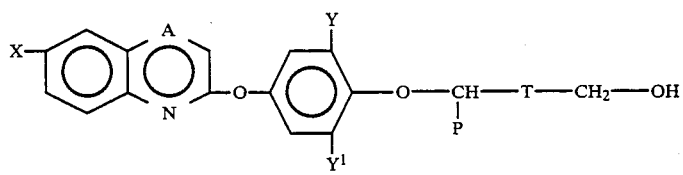

(I)

wherein
Y and $Y^1$ each independently represent —H or —F;
P represents methyl or ethyl;
T represents $-(CH_2-CH_2)_a(CH=CH)_b$ and the cis (Z) or trans (E) stereoisomers thereof or $-(CH_2-CH_2)_a-(C\equiv C)$;
A represents $\equiv N$ or $\equiv CH$;
a represents the integer 0, 1 or 2;
b represents the integer 1 or 2; and
X represents —Br, —Cl, —F or —CF$_3$.

The term "C$_1$-C$_4$ alkyl" as employed in the present specification and claims designates alkyl groups which can be straight or branched chain containing from 1 to 4 carbon atoms or cycloalkyl of 3 or 4 carbon atoms.

In the present invention, it is to be noted that all substituent groups are sterically compatible with each other. The term "sterically compatible" is employed to designate substituent groups which are not affected by steric hindrance as this term is defined in "The Condensed Chemical Dictionary", 7th edition, Reinhold Publishing Co., N.Y., page 893 (1966) which definition is as follows:

"steric hindrance. A characteristic of molecular structure in which the molecules have a spatial arrangement of their atoms such that a given reaction with another molecule is prevented or retarded in rate."

Sterically compatible may be further defined as reacting compounds having substituents whose physical bulk does not require confinement within volumes insufficient for the exercise of their normal behavior as discussed in "Organic Chemistry" of D. J. Cram and G. Hammond, 2nd edition, McGraw-Hill Book Company, N.Y., page 215 (1964).

The compounds of the present invention contain the optically active center

and can exist in optically active stereoisomeric forms such as the R and S enantiomeric forms. The use of the various mixtures and racemates of the above isomers are within the scope of the present invention. Additionally, the R enantiomer of such compounds have been found to be more active biologically than the S enantiomer and may be used whenever the greater activity justifies the extra expenses for the use of this isomer.

In addition, the compounds of the present invention can contain isomers of the geometric isomer class which result from a carbon-carbon double bond. The resulting isomers are called cis (Z) and trans (E) isomers.

A general discussion of the isomer activity difference phenomenon can be found in A. Albert, Selective Toxicity, 4th edition, Met Luen & Co., Ltd., London, 1968, pp. 387-390 and more particular discussions in A. Fredga and B. Åberg, "Stereoisomerism in plant growth regulators of the auxin type", Ann. Rev. Plant Physiology 16:53-72, 1965, and in E. J. Lien, J. F. R. DeMiranda and E. J. Airens, "Quantitative structure-activity correlation of optical isomers", Molecular Pharmacology 12:598-604, 1976.

The compounds of the present invention are generally oils or low melting crystalline solids at ambient temperatures which are soluble in many organic solvents.

Representative compounds of the present invention are set forth below in Table 1.

TABLE 1

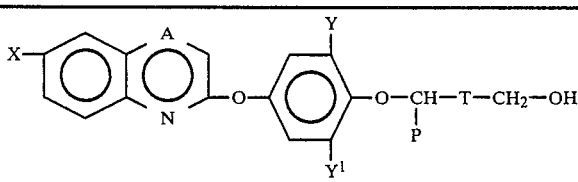

| A   | X    | Y  | Y¹ | P      | T                |
|-----|------|----|----|--------|------------------|
| ≡CH | —F   | —H | —H | —C₂H₅  | $-(CH=CH)_2$     |
| ≡N  | —Cl  | —H | —H | —CH₃   | —CH=CH—          |
| ≡CH | —Br  | —H | —H | —CH₃   | —CH=CH—          |
| ≡N  | —F   | —H | —H | —CH₃   | —CH=CH—          |
| ≡N  | —Cl  | —H | —H | —C₂H₅  | —CH=CH—          |
| ≡N  | —CF₃ | —H | —H | —CH₃   | —CH=CH—          |
| ≡CH | —Cl  | —H | —H | —CH₃   | $-(CH=CH)_2$     |
| ≡N  | —Cl  | —H | —H | —CH₃   | $-(CH=CH)_2$     |
| ≡N  | —F   | —H | —H | —CH₃   | $-(CH=CH)_2$     |
| ≡CH | —CF₃ | —H | —H | —C₂H₅  | $-(CH=CH)_2$     |
| ≡N  | —CF₃ | —H | —H | —CH₃   | $-(CH=CH)_2$     |
| ≡N  | —Cl  | —F | —H | —CH₃   | —CH=CH—          |
| ≡N  | —F   | —H | —F | —CH₃   | —CH=CH—          |
| ≡N  | —Cl  | —F | —H | —C₂H₅  | —CH=CH—          |
| ≡CH | —Cl  | —F | —F | —C₂H₅  | $-(CH_2CH_2)_2-(CH=CH)_2$ |
| ≡N  | —Cl  | —H | —H | —C₂H₅  | $-(CH=CH)_2$     |
| ≡N  | —CF₃ | —H | —H | —C₂H₅  | —CH=CH—          |
| ≡CH | —Cl  | —H | —H | —CH₃   | —CH=CH—          |
| ≡CH | —Cl  | —F | —H | —C₂H₅  | —CH=CH—          |
| ≡CH | —F   | —F | —F | —CH₃   | —CH=CH—          |
| ≡CH | —Cl  | —F | —F | —CH₃   | —CH=CH—          |

The 4-((aryloxy)phenoxy)alkenols of the present invention corresponding to the formula

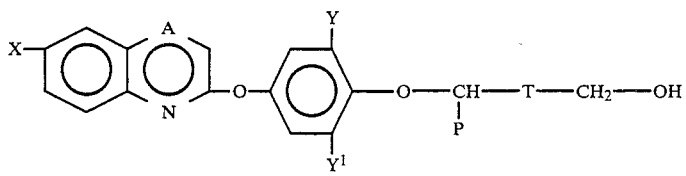
(I)

can be prepared by the reaction of substantially equimolar amounts of an appropriate compound corresponding to the formula

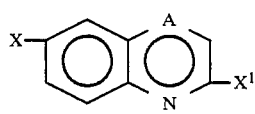
(II)

wherein X and A are as hereinbefore defined and X¹ represents —Br, —Cl, —F or —SO₂R¹ and R¹ is C₁-C₄ alkyl with an appropriate alkenol derivative corresponding to the formula

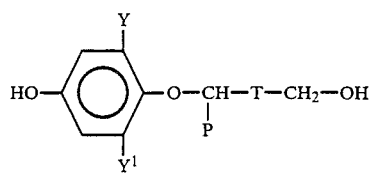
(III)

wherein Y, Y¹, P and T are as hereinbefore defined. In carrying out this reaction, the reactants and a strong base such as an anhydrous alkali metal hydride, alkoxide, hydroxide or carbonate are mixed together in a dipolar, aprotic solvent such as, for example, dimethylformamide (DMF), acetone, methyl ethyl ketone, acetonitrile, dimethylsulfoxide (DMSO), sulfolane, N-methylpyrrolidone or the like. The reaction is advantageously carried out at elevated temperatures of from about 50° to 120° C.

The specific reaction times employed in the hereinabove and hereinafter set forth preparative procedures vary considerably and are dependent upon factors such as the solvent, base, catalyst, if employed, reaction temperature and the reactivity of the specific reactants employed. The reactions are for the most part complete in a period of from about 30 minutes to about 12 hours or This procedure is also the preferred procedure to use when Y and Y¹ are both fluorine.

The compound of Formula I wherein Y and Y¹ are both hydrogen and A is ≡CH can also be prepared by the reaction of an appropriate aryloxyphenol corresponding to the formula

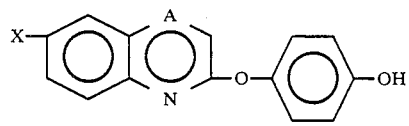
(IV)

an appropriate α-haloalkenoic acid ester corresponding to the formula

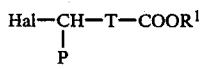

wherein P, R¹ and T are as hereinbefore defined, and Hal is —Cl or —Br employing the same reaction conditions as set forth hereinabove for the reaction between the reactants of Formulae II and III.

The ester product corresponding to the formula

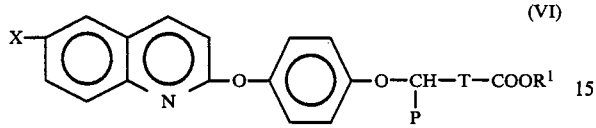

is reduced to the corresponding 4-((aryloxy)phenoxy)alkenol of Formula I. The reduction of the ester of Formula VI is conveniently carried out by reaction of said ester with a reducing agent such as, for example, diisobutylaluminum hydride (DIBAL-H) or lithium aluminum hydride (LAH) in an inert solvent. The solvent and reaction temperature employed depend primarily upon the specific reducing agent. When DIBAL-H is employed, the reaction temperature is within the range of about −78° to about +25° C. and the solvents include toluene, ether or cyclohexane. When LAH is employed, the reaction is conducted by refluxing the ester in a solvent such as ether or tetrahydrofuran.

The hydroxyphenoxy alkenols corresponding to the formula

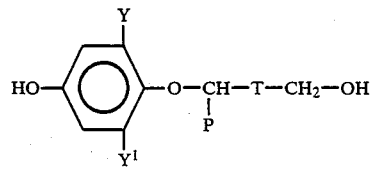

are prepared by a variety of procedures. Those compounds wherein Y and Y¹ are both hydrogen, are for the most part known compounds and are taught in U.S. Pat. Nos. 4,263,040 and 4,360,375; and Japanese Kokai Nos. J56034-647 and J56034-648.

Those compounds of Formula III wherein Y and/or Y¹ are fluorine can be prepared in a multistep procedure as follows:

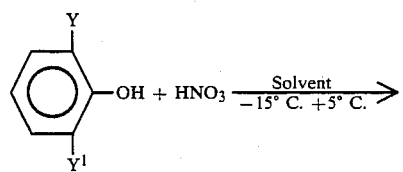

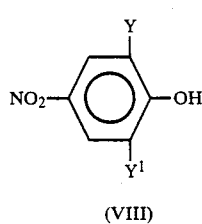

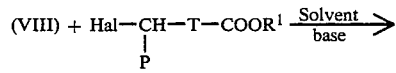

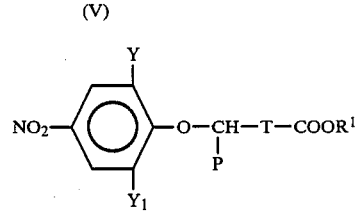

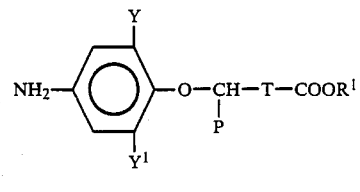

1. HCl
2. NaNO₂
3. HBF₄

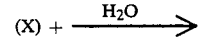

(XI)

1. CF₃COOH
   base
2. Acid
   Solvent
   Δ

(XII) + ─────────→

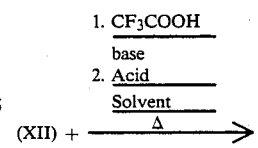

(XII)

No attempt has been made to present a balanced equation the above reaction sequence.

The above reaction steps can be carried out as follows:

Step A

The appropriate fluorophenol of Formula VII in a solvent such as, for example, methylene chloride is reacted for from about 1 to about 3 hours with 90 percent nitric acid at a temperature of from about −15° C. to about 5° C. At the end of this period, the desired 2-fluoro- or 2,6-difluoro-4-nitrophenol product of For-

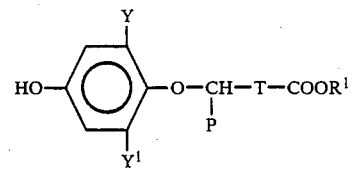

mula VIII is recovered employing conventional procedures.

Step B

The thus formed 2-fluoro- or 2,6-difluoro-4-nitrophenol of Formula VIII is reacted with an appropriate α-alkenoic acid ester, corresponding to Formula V. In carrying out this reaction, the compound of Formula V, the phenol compound of Formula VIII and a base metallic base such as sodium or potassium carbonate, or an organic base such as triethylamine are mixed together in the presence of a solvent such as dimethylsulfoxide (DMSO), dimethylformamide, tetrahydrofuran, acetonitrile, hexamethylphosphoramide or N-methylpyrrolidone and heated to a temperature between about 40° C. to about 220° C. The desired fluorinated 4-nitrophenoxy alkenoic acid ester corresponding to Formula IX is recovered employing conventional procedures.

Step C

The thus formed fluorinated 4-nitrophenoxyalkenoic acid ester corresponding to Formula IX is selectively reduced to the corresponding amino (aniline) compound corresponding to Formula X. This reduction can be conveniently carried out employing conventional stannous chloride reduction procedure. The product is recovered employing conventional recovery procedures.

Step D

The thus formed aniline compound corresponding to Formula X is treated with an aqueous solution of concentrated HCl at a temperature of from about 0°–10° C. and this solution is then reacted with an aqueous solution of an alkali metal nitrite. This mixture is thereafter reacted with an aqueous solution of fluoroboric acid to form the desired corresponding diazonium tetrafluoroborate compound corresponding to Formula XI. The product is separated employing conventional procedure.

Step E

The thus formed compound corresponding to Formula X is treated under reflux conditions with a mixture of an alkali metal trifluoroacetate in trifluoroacetic acid to obtain the desired product compound corresponding to Formula XII.

The hydroxyphenoxy alkenoic acid ester corresponding to Formula XII can then be reduced to the corresponding hydroxyphenoxyalkenol of Formula III employing the procedure set forth hereinabove employed for reducing the compound of Formula VI to the compound of Formula I.

The heterocyclic halides employed as starting materials and which correspond to the formula

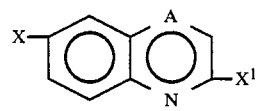

wherein A, X and $X^1$ are as hereinbefore defined, are all known and/or commercially produced compounds and for the most part are taught in the above-listed applications and/or patents which teach preparing compounds of 5 Formula IV.

The α-haloalkenoic acid esters employed as a starting material and corresponding to the formula

wherein Hal, P, $R^1$ and T are as hereinbefore defined are all known compounds and such compounds are taught in European Patent Application No. 42750.

The following examples illustrate the present invention and the manner by which it can be practiced but, as such, are not to be construed as limitations upon the overall scope thereof.

The compounds obtained in the following examples were characterized by infrared and/or nuclear magnetic resonance spectrometry.

EXAMPLE 1

E isomer of 4-(4-hydroxyphenoxy)-2-penten-1-ol

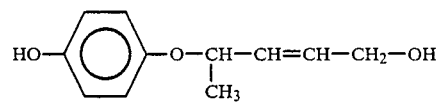

An oven-dried flask was equipped with a nitrogen inlet, a stirrer, a thermometer and a septum stoppered dropping funnel and was flushed with nitrogen. The flask was charged with a solution of 26.6 grams (g) (120 millimole (mmol)) of methyl (E)-4-(4-hydroxyphenoxy)-2-pentenoate in 150 milliliters (ml) of toluene. The solution was cooled to −78° C., and the dropping funnel was charged with 250 ml (375 mmol) of 25 percent (%) solution of diisobutylaluminum hydride (DIBAL) in toluene. The DIBAL solution was then added at −78° C. dropwise to the reaction mixture over a 1.5 hour period, and the reaction was stirred at −78° C. for an additional 0.5 hour. The reaction was quenched by cautious, dropwise addition of 250 ml of a stock solution prepared from 6 parts of water, 25 parts of acetic acid and 75 parts of ether while maintaining the temperature below −50° C. The resulting mixture was allowed to warm to room temperature and filtered, and the solid was washed with ether. The filtrates were combined and reserved while the solid was partitioned between water and ether.

This mixture was made acidic with aqueous HCl, and the ether layer separated and combined with the reserved filtrates. The combined organic solution was then washed to neutrality with saturated aqueous sodium bicarbonate, dried over MgSO$_4$ and evaporated to dryness. The oily residue was then purified by preparative scale liquid chromatography (HPLC) eluting with 3:2 hexane: acetone removal of solvent and through drying left 19.3 g (83%) of the desired alcohol as a tan oil. (Compound A).

| | Elemental Analysis: | |
|---|---|---|
| | % C | % H |
| Calculated for $C_{11}H_{14}O_3$: | 68.02 | 7.26 |
| Found: | 67.24 | 7.26 |

EXAMPLE 2

E-isomer of 4-(4-((6-chloro-2-quinolinyl)oxy)phenoxy)-2-penten-1-ol

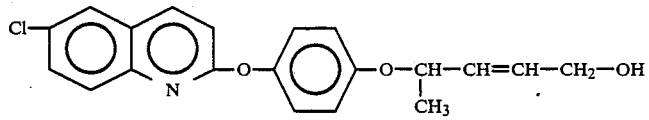

A mixture of 3.06 g (15.4 mmol) of 2,6-dichloroquinoline, 3.00 g (15.4 mmol) of (E)-4-(4-hydroxyphenoxy)-2-penten-1-ol, 2.34 g (16.9 mmol) of powdered, anhydrous potassium carbonate and 50 ml of dry dimethylsulfoxide was warmed at 100°-110° C. for a period of 6 hours. The mixture was cooled to room temperature, poured over ice and extracted three times with ether. The combined ether layers were washed once with 1 percent aqueous sodium hydroxide then with water, dried over MgSO4 and evaporated to dryness. The residue was purified by preparative scale HPLC, eluting with 72:28 hexane:acetone, and then thoroughly dried to leave 2.9 g of the desired pentenol as a brown gum. (Compound B).

| Elemental Analysis: | | | |
|---|---|---|---|
| | % C | % H | % N |
| Calculated for $C_{20}H_{18}ClNO_3$: | 67.51 | 5.10 | 3.94 |
| Found: | 67.11 | 5.24 | 3.78 |

EXAMPLE 3

E isomer of 4-(4-((6-chloro-2-quinoxalinyl)oxy)phenoxy)2-penten-1-ol

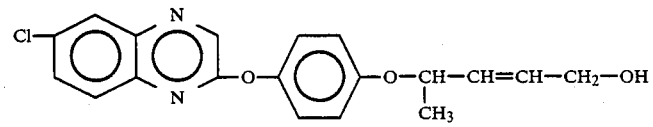

A mixture of 1.99 g (10 mmol) of 2,6-dichloroquinoxaline, 2.13 g (11 mmol) of 4-(4-hydroxyphenoxy)-2-penten-1-ol, 1.73 g (12.5 mmol) of powdered, anhydrous potassium carbonate and 50 ml of dry acetonitrile was warmed at reflux under nitrogen for a period of 3 hours. The mixture was cooled to room temperature, and the solid filtered off and washed well with ether. The filtrates were combined and evaporated to dryness, and the residue partitioned between ether and 2 percent aqueous sodium hydroxide. The aqueous layer was separated and extracted again with ether. The combined organic layers were washed with water, dried over MgSO4 and evaporated to dryness. The residual solid was purified by preparative scale HPLC, eluting with 7:3 hexane:ethyl acetate, to give a solid which was recrystallized from toluene. This gave 2.60 g (73%) of the desired pentenol as pale yellow crystals, having a melting point (m.p.) of 124°-126° C. (Compound C).

| Elemental Analysis: | | | |
|---|---|---|---|
| | % C | % H | % N |
| Calculated for $C_{19}H_{17}ClN_2O_3$: | 63.95 | 4.80 | 7.85 |
| Found: | 63.73 | 4.75 | 7.81 |

EXAMPLE 4

4-(4-((6—Bromo-2-quinoxalinyl)oxy)phenoxy)-2-penten-1-ol

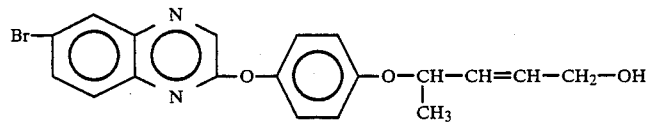

A mixture of 3.76 g (15.4 mmol) of 6-bromo-2-chloroquinoxaline, 3.00 g (15.4 mmol) of 4-(4-hydroxyphenoxy)-2-penten-1-ol, 2.34 g (16.9 mmol) of powdered, anhydrous potassium carbonate and 50 ml of dry dimethylsulfoxide was stirred at room temperature for a period of 24 hours. The mixture was poured over ice and extracted three times with ether. The combined ether layers were washed with 1 percent aqueous sodium hydroxide, then with water, dried over MgSO4 and evaporated to dryness. The residue was recrystallized from toluene to give 2.50 g of the desired pentenol as a yellow solid. (Compound D).

| Elemental Analysis: | | | |
|---|---|---|---|
| | % C | % H | % N |
| Calculated for $C_{19}H_{17}BrN_2O_3$: | 56.87 | 4.27 | 6.98 |
| Found: | 57.06 | 4.33 | 6.79 |

EXAMPLE 5

4-(4-((6-Fluoro-2-quinolinyl)oxy)phenoxy)-2-penten-1-ol

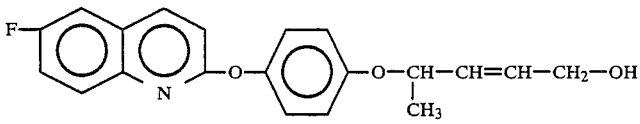

A mixture of 3.63 g (20 mmol) of 2-chloro-6-fluoroquinoxaline, 4.27 g (22 mmol) of 4-(4-hydroxyphenoxy)-2-penten-1-ol, 3.31 g (24 mmol) of powdered, anhydrous potassium carbonate and 30 ml of dry dimethylsulfoxide was warmed at 120° C. for a period of 5 hours. The mixture was cooled to room temperature, poured over dilute aqueous HCl, and the resulting aqueous mixture was extracted two times with ether. The combined ether layers were washed twice with 5 percent aqueous sodium hydroxide, then with water, dried over MgSO4 and evaporated to dryness. The residue was purified by preparative scale HPLC, eluting with 4:1:hexane:acetone, and then thoroughly dried to give 2.44 g of the desired pentenol as a tan gum. (Compound E).

| Elemental Analysis: | | | |
|---|---|---|---|
| | % C | % H | % N |
| Calculated for $C_{20}H_{18}FNO_3$: | 70.78 | 5.35 | 4.13 |
| Found: | 70.09 | 5.23 | 4.16 |

EXAMPLE 6

4-(4-((6-Fluoro-2-quinoxalinyl)oxy)phenoxy)-2-penten-1-ol

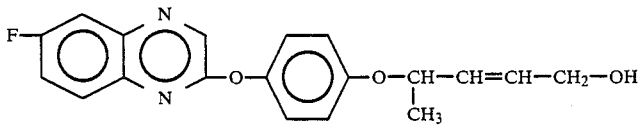

A mixture of 1.28 g (7 mmol) of 2-chloro-6-fluoroquinoxaline, 1.16 g (8.4 mmol) of anhydrous, powdered potassium carbonate, 1.55 g (8 mmol) of 4-(4-hydroxyphenoxy)-2-penten-1-ol and 20 ml of DMSO was warmed, under nitrogen, at 110° C. for a period of 2 hours. The mixture was cooled to room temperature, poured into dilute, aqueous HCl and extracted with two portions of ether. The combined organic layers were washed twice with 1 percent aqueous NaOH and with water, dried over MgSO4 and evaporated to dryness. The residue was purified by preparative scale HPLC, eluting with 3:1 hexane:acetone. After removal of solvent the resulting tan crystals were recrystallized from methylcyclohexane to give 1.05 g of crystals which were further purified by recrystallization from toluene to leave nearly colorless crystals, m.p. 109°–111° C. (Compound F)

| Elemental Analysis | | | |
|---|---|---|---|
| | % C | % H | % N |
| Calculated for $C_{19}H_{17}FN_2O_3$: | 67.05 | 5.04 | 8.23 |
| Found: | 66.04 | 5.07 | 8.01 |

As indicated hereinabove, the novel 4-((aryloxy)phenoxy)alkenols of the present invention are herbicides and are useful in controlling grassy weeds and especially controlling grassy weeds in the presence of broadleaf crop plants both pre- and postemergently.

The alkenols of the present invention are also useful as intermediates in the preparation of herbicidally active derivatives. These so prepared derivatives correspond to the formula

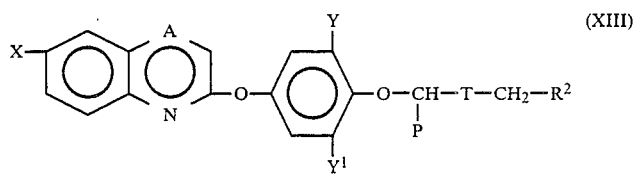

(XIII)

wherein
Y and $Y^1$ each independently represent —H or —F;
P represents methyl or ethyl;
T represents $-(CH_2-CH_2)_a-(CH=CH)_b-$ and the cis (Z) or trans (E) stereoisomers thereof or $-(CH_2-CH_2)_a-(C\equiv C)-$;
A represents $\equiv$N or $\equiv$CH;
a represents the integer 0, 1 or 2;
b represents the integer 1 or 2;
X represents —Br, —Cl, —F, or —CF3;
$R^2$ represents —OSO2$R^3$,

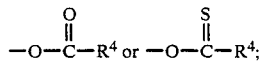

$R^3$ represents $C_1-C_4$ alkyl, $C_2-C_4$ alkenyl or $NR^4R^5$;
$R^4$ represents $C_2-C_4$ alkenyl, $C_1-C_4$ alkyl, —$NR^5R^6$ or

wherein $R^5$ and $R^6$ each independently represent —H or $C_1$-$C_4$ alkyl;

D represents $C_1$-$C_4$ alkyl, —Br, —Cl, —$NO_2$, —$CF_3$, ence of an inert solvent and a hydrogen halide absorber (acid scavenger) to obtain the desired compound corresponding to the formula

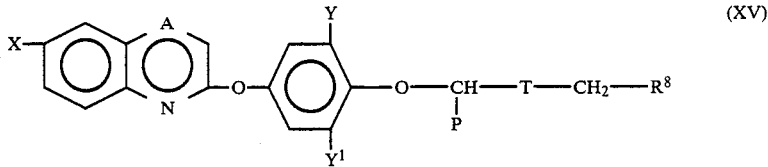

(XV)

—$OCF_3$,

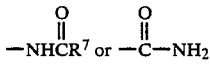

wherein $R^7$ represents $C_1$-$C_4$ alkyl and m represents an integer of from 0-3, inclusive.

The above active derivative compounds have been found to be useful as herbicides for the postemergent kill and control of undesirable vegetation, for example, grassy or graminaceous weeds in the presence of corn plants.

The term "herbicide" is used herein to mean an active ingredient which controls or adversely modifies the growth of plants because of phytotoxic or other effects substantial enough to seriously retard the growth of the plant or further to damage the plant sufficiently to kill the plant.

The terms "growth controlling" or "herbicidally effective" amount are employed to designate an amount of active ingredient which causes a modifying effect and includes deviations from natural development, killing, regulation, dessication, retardation, and the like.

The term "plants" means established vegetation.

The terms "control" or "controlling" as it relates to plant growth has the same meaning as employed hereinabove for the term "herbicide".

The derivative compounds wherein $R^2$ is

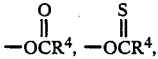

or —$OSO_2R^3$ and $R^3$ and $R^4$ are other than —$NHR^6$ can be prepared by the condensation of an appropriate 4-((aryloxy)phenoxy)alkenol corresponding to the formula

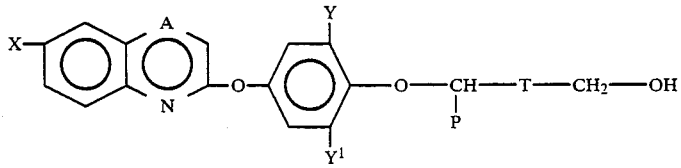

with an appropriate halide corresponding to the formula

Hal—$R^8$ (XIV)

wherein $R^8$ is 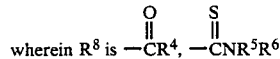

or —$SO_2R^3$ and $R^3$, $R^4$ is as further defined directly hereinabove and $R^5$ is other than hydrogen in the preswherein in Formulae I, XIV and XV; A, X, Y, $Y^1$, P, $R^2$, T and Hal are as hereinabove defined.

The reaction is generally carried out at a temperature in the range of from about 0° to about 25° C.

While not normally necessary, a catalyst can be employed, if desired. Representative catalysts include, for example, 4-dimethylaminopyridine and 1,4-diazabicyclo-2,2,2-octane.

Representative inert solvents for this reaction include, for example, chlorinated hydrocarbons (for example, methylene chloride), ether, toluene, pyridine, hexane, acetonitrile and the like.

Representative hydrogen halide absorbers include tertiary amines, alkali metal hydroxides and alkali metal carbonates. Alternatively, it has also been found that the addition of a molar excess of the amine reactant can function as the hydrogen halide absorber. Additionally, when pyridine is employed as the solvent, it can also function as the hydrogen halide absorber.

Additionally, when $R^2$ is

and $R^4$ is other than —$NR^5R^6$, an appropriate anhydride corresponding to the formula

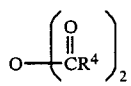

(XVI)

wherein $R^4$ is as hereinbefore defined can be reacted with the alkenol corresponding to Formula I employing the same procedure and conditions as set forth hereinabove for the reaction between the reactants of Formulae I and XIV.

—O—CH—T—$CH_2$—OH (I)

(with P below CH, $Y^1$ on ring)

Further, when $R^2$ is

and $R^4$ is $C_2$—$C_4$ alkenyl or $C_1$-$C_4$ alkyl, an appropriate ester corresponding to the formula ((aryloxy)phenoxy)alkenol corresponding to the formula

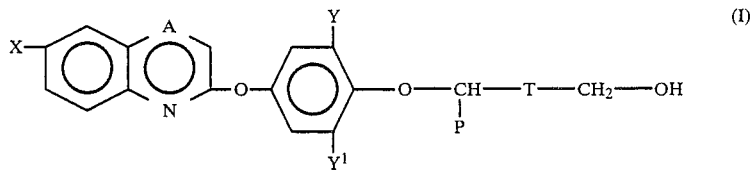
(I)

(XVII)

wherein P is as hereinbefore defined and $R^9$ is $C_2$-$C_4$ or $C_1$-$C_4$ alkyl is reacted with the alkenol corresponding to Formula I employing the same procedure and conditions as set forth hereinabove for the reaction between the reactants of Formulae I and XIV.

The derivative compounds wherein $R^2$ is

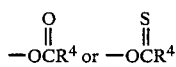

and $R^4$ are $-NHR^6$ can be prepared by the condensation of an appropriate alkenol of Formula I with an appropriate isocyanate or isothiocyanate corresponding to the formula $$R^6NC{=}O/S \qquad (XVIII)$$

wherein $R^6$ is as hereinbefore defined. The reaction is generally carried out in the presence of an inert solvent such as methylene chloride or toluene at ambient temperatures, though the use of higher temperatures could be necessary depending on the $S/O{=}CNR^6$ reactant to effect condensation. A catalytic amount of a base such as, for example, triethylamine, is sometimes beneficial. The isocyanate reactants are all known compounds of commerce.

The derivative compounds which correspond to the formula wherein P, A, X, Y, $Y^1$ and T are as hereinbefore set forth with an appropriate substituted benzoic acid corresponding to the formula

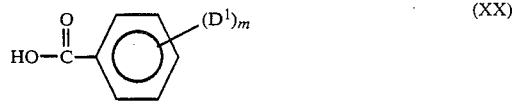
(XX)

wherein $D^1$ and m are as hereinbefore set forth in the presence of a solvent such as DMF, methylene chloride or ether and in the presence of a catalyst such as 4-(dimethylamino)pyridine and an aid for forming esters at low temperatures. Representative of such agents are carbodiimides such as dicyclohexylcarbodiimide.

The desired product can be separated from the reaction mixture of the above preparative procedures employing conventional separatory procedures known to those skilled in the art including steps of solvent extraction, filtration, water washing, column chromatography, neutralization, acidification, crystallization and distillation.

Since the hereinabove and hereinafter set forth compound preparation procedures employ only standard chemistry practices, and it is known that slightly different reactants can require slightly different reaction parameters from those for other reactants, it is to be understood that minor modifications to the reaction parameters set forth such as the use of an excess of one reactant, the use of a catalyst, the use of high temperature and/or pressure equipment, high speed mixing and

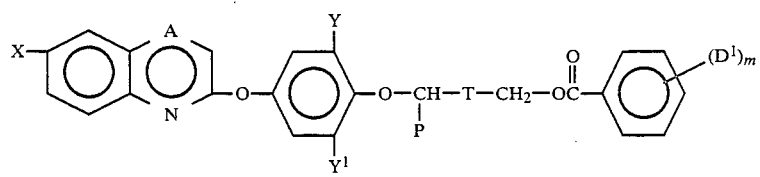
(XIX)

wherein P, A, X, Y, $Y^1$, T and m are as hereinbefore set forth and $D^1$ is

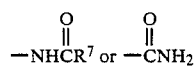

and $R^7$ is as hereinbefore defined, can be prepared reaction, at ambient temperature, of an appropriate 4- other such conventional changes are within the scope of this invention.

The following examples further illustrate the present invention and the manner by which it can be practiced.

EXAMPLE 7

E isomer of 4-(4-(((6-chloro-2-quinolinyl)oxy)phenoxy-2-penten-1-ol, 1-methylethyl sulfonate

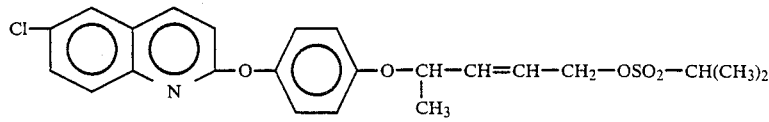

A solution prepared from 1.07 g (3 mmol) of the pentenol obtained in Example 2, 0.40 g (4 mmol) of triethylamine, and 20 ml of methylene chloride was cooled at 0° C. under nitrogen and a solution of 0.50 g (3.5 mmol) of isopropylsulfonylchloride in 3 ml of methylene chloride was added in one portion. The resulting solution was stirred at 0° C. for 30 minutes and then poured into a mixture of ether and about 1N aqueous HCl. The organic layer was separated, dried over MgSO4 and evaporated to dryness. The residue was purified by preparative scale HPLC, eluting with 3:1 hexane:ethyl acetate, and then dried in a Kugelrohr apparatus at 50° C. and 0.1 mm Hg for hour. This left 1.31 g (95%) of desired sulfonate product as a viscous oil. (Compound 1).

| Elemental Analysis: | % C | % H | % N |
|---|---|---|---|
| Calculated for $C_{23}H_{24}ClNO_5S$: | 59.80 | 5.24 | 3.03 |
| Found: | 58.91 | 5.11 | 2.90 | cooled under $N_2$ at 0° C. while 0.78 g (5.5 mmol) of isopropylsulfonylchloride was added in one portion. After stirring at 0° C. for 45 minutes, the mixture was poured into a mixture of ether and water. The organic layer was separated, dried over MgSO4 and evaporated to dryness. The residual solid was taken up in boiling hexane, filtered while hot and allowed to cool to give pale yellow crystals. The crystals were filtered and dried to give 1.65 g (71%) of the desired sulfonate product, m.p. 95°–96° C. (Compound 2).

| Elemental Analysis: | % C | % H | % N |
|---|---|---|---|
| Calculated for $C_{22}H_{23}ClN_2O_5S$: | 57.07 | 5.01 | 6.05 |
| Found: | 56.78 | 4.92 | 5.96 |

By following the procedure of Examples 4 and 5 employing the appropriate starting pentenols and sulfonyl or sulfamoyl halides, the following compounds in Table 2 are prepared.

TABLE 2

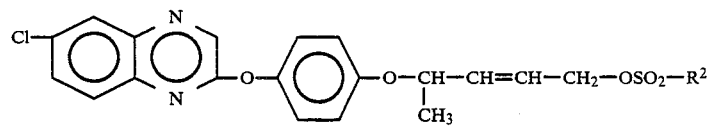

| Compound No. | $R^2$ | M.P. °C. or RI at ($n_D^{25}$) | Molecular Formula and Elemental Analysis | | | |
|---|---|---|---|---|---|---|
| | | | | % C | % H | % N |
| 3 | —NHCH(CH3)2 | 73–75 | $C_{22}H_{24}ClN_3O_5S$ Calc: | 55.28 | 5.06 | 8.79 |
| | | | Found: | 55.59 | 5.09 | 8.68 |
| 4 | —CH3 | 115–116 | $C_{20}H_{19}ClN_2O_5S$ Calc: | 55.23 | 4.40 | 6.44 |
| | | | Found: | 54.94 | 4.30 | 6.34 |
| 5 | —C2H5 | 95–97 | $C_{21}H_{21}ClN_2O_5S$ Calc: | 56.18 | 4.72 | 6.24 |
| | | | Found: | 56.27 | 4.58 | 6.14 |
| 6 | —C3H7 | 81–83 | $C_{22}H_{23}ClN_2O_5S$ Calc: | 57.07 | 5.01 | 6.05 |
| | | | Found: | 56.44 | 4.91 | 5.94 |
| 7 | —C4H9 | 85–87 | $C_{23}H_{25}ClN_2O_5S$ Calc: | 57.91 | 5.28 | 5.87 |
| | | | Found: | 57.89 | 5.16 | 5.71 |

EXAMPLE 8

E isomer of 4-(4-((6-chloro-2-quinoxalinyl)oxy)phenoxy)-2-penten-1-ol, 1-methylethyl sulfonate

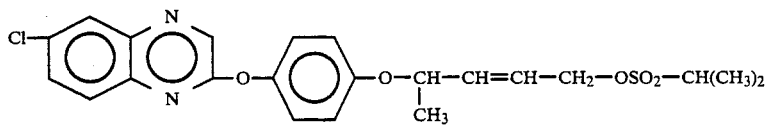

A solution prepared from 1.78 g (5 mmol) of the pentenol obtained in Example 3 above, 0.61 g (6 mmol) of triethylamine and 25 ml of methylene chloride was

EXAMPLE 9

E isomer of 4-(4-((6-chloro-2-quinoxalinyl)oxy)phenoxy)-2-penten-1-ol, acetate

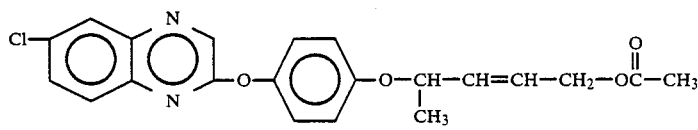

To an ice-cooled nitrogen flushed solution of 1.78 g (5 mmol) of the pentenol obtained in Example 3 above in 10 ml of pyridine was added 0.61 g (6 mmol) of acetic anhydride. The resulting solution was allowed to warm to room temperature and stirred under nitrogen overnight. The solution was then poured into a mixture of ether and water. The organic layer was separated and washed three times with 2 percent aqueous HCl and saturated aqueous NaHCO$_3$, dried over MgSO$_4$ and evaporated to leave an off-white solid. The solid was purified by filtration, using methylene chloride as the solvent, through a short plug of silica gel, and then, after removal of solvent, recrystallized from methylcyclohexane. This gave colorless crystals which were filtered, washed with hexane and dried to give 1.27 g (64%) of the desired acetate as colorless crystals, m.p. 89°–90° C. (Compound 8).

| Elemental Analysis: | | | |
|---|---|---|---|
| | % C | % H | % N |
| Calculated for C$_{21}$H$_{19}$ClN$_2$O$_4$: | 63.24 | 4.80 | 7.03 |
| Found: | 62.49 | 4.70 | 6.89 |

A nitrogen flushed solution of 1.78 g (5 mmol) of the pentenol obtained in Example 3 in 20 ml of pyridine was cooled in an ice bath and 0.77 g (5.5 mmol) of benzoylchloride was slowly added. The resulting mixture was stirred at 0° C. for 1 hour and then at ambient temperature for 2 hours. The reaction mixture was then poured into a mixture of water and ether. The organic layer was separated, washed twice with 1N aqueous HCl and then with saturated aqueous NaHCO$_3$, dried over MgSO$_4$ and evaporated to dryness. After standing at room temperature, the residue slowly crystallized and the solid was recrystallized from methylcyclohexane to give, after filtering and drying, 1.90 g (82%) of the desired benzoate as colorless crystals melting at 79°–81° C. (Compound 9).

| Elemental Analysis: | | | |
|---|---|---|---|
| | % C | % H | % N |
| Calculated for C$_{26}$H$_{21}$ClN$_2$O$_4$: | 67.75 | 4.59 | 6.08 |
| Found: | 67.56 | 4.49 | 6.08 |

EXAMPLE 10

E isomer of 4-(4-((6-chloro-2-quinoxalinyl)oxy)phenoxy)-2-penten-1-ol, benzoate

By substantially following the procedures of Example 6 employing the appropriate starting pentenols and acid halide in pyridine, the following compounds in Table 3 are prepared.

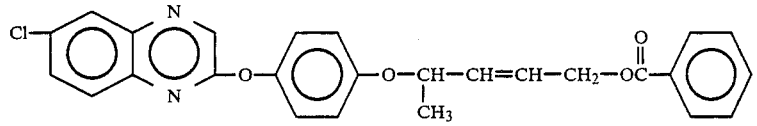

TABLE 3

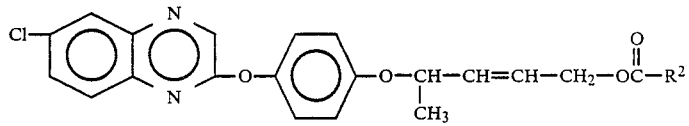

| Compound No. | R$^2$ | M.P. °C. or RI at (n$_D^{25}$) | Molecular Formula and Elemental Analysis | | | |
|---|---|---|---|---|---|---|
| | | | | % C | % H | % N |
| 10 | —C(CH$_3$)$_3$ | 86–88 | C$_{24}$H$_{25}$ClN$_2$O$_4$ | | | |
| | | | Calc: | 65.37 | 5.72 | 6.35 |
| | | | Found: | 65.39 | 5.72 | 6.28 |
| 11 | —C$_6$H$_4$—CF$_3$ | 71–75 | C$_{27}$H$_{20}$CF$_3$N$_2$O$_4$ | | | |
| | | | Calc: | 61.31 | 3.81 | 5.30 |
| | | | Found: | 61.32 | 3.82 | 5.61 |
| 12 | —CH(CH$_3$)$_2$ | 45–49 | C$_{23}$H$_{23}$ClN$_2$O$_4$ | | | |
| | | | Calc: | 64.71 | 5.43 | 6.56 |
| | | | Found: | 64.51 | 5.37 | 6.63 |
| 13 | —C$_3$H$_7$ | yellow oil | C$_{23}$H$_{23}$ClN$_2$O$_4$ | | | |
| | | | Calc: | 64.71 | 5.43 | 6.56 |
| | | | Found: | 64.55 | 5.46 | 6.76 |
| 14 | —C$_6$H$_4$—OCF$_3$ | 80–84 | C$_{27}$H$_{20}$ClF$_3$N$_2$O$_5$ | | | |
| | | | Calc: | 59.51 | 3.70 | 5.14 |
| | | | Found: | 59.10 | 3.68 | 5.29 |
| | | | C$_{27}$H$_{23}$ClN$_2$O$_4$ | | | |

TABLE 3-continued

[Structure: 6-chloro-quinoxalinyl-O-phenyl-O-CH(CH3)-CH=CH-CH2-OC(=O)-R²]

| Compound No. | R² | M.P. °C. or RI at (nD²⁵) | Molecular Formula and Elemental Analysis | | |
|---|---|---|---|---|---|
| | | | | % C | % H | % N |
| 15 | –⟨phenyl⟩–CH₃ | 70–74 | Calc: | 68.28 | 4.88 | 5.90 |
| | | | Found: | 68.25 | 4.88 | 5.95 |
| 16 | –⟨phenyl⟩–C₂H₅ | 87–89 | $C_{28}H_{25}ClN_2O_4$ | | | |
| | | | Calc: | 68.78 | 5.15 | 5.73 |
| | | | Found: | 68.59 | 5.20 | 5.92 |
| 17 | –⟨phenyl⟩–NO₂ | 99–103 | $C_{26}H_{20}ClN_3O_6$ | | | |
| | | | Calc: | 61.73 | 3.98 | 8.31 |
| | | | Found: | 62.13 | 4.11 | 8.28 |

EXAMPLE 11

E isomer of 4-(4-((6-chloro-2-quinoxalinyl)oxy)phenoxy)-2-penten-1-ol, 4-chlorobenzoate

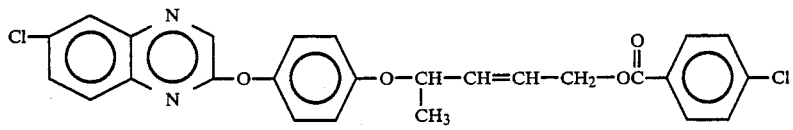

A nitrogen flushed solution of 1.78 g (5 mmol) of the pentenol obtained in Example 3 above, 0.61 g (6 mmol) of triethylamine and 40 ml of methylene chloride was cooled in an ice bath. A solution of 1.05 g (6 mmol) of 4-chlorobenzoyl chloride in 2 ml of methylene chloride was slowly added, and the resulting solution allowed to stir at ambient temperature overnight. The mixture was then poured into water, and the organic layer separated and washed with saturated aqueous NaHCO₃ and saturated aqueous NaCl, dried over MgSO₄ and evaporated to leave an oil. The oil was purified by preparative scale HPLC, eluting with 85:15 hexane:ethyl acetate. After removal of the solvent, an oil was obtained which, after trituration with hexane, solidified. The solid was filtered, washed with hexane and dried to give 1.91 g (77%) of the desired ester melting at 96°–99° C. (Compound 18).

| Elemental Analysis: | % C | % H | % N |
|---|---|---|---|
| Calculated for $C_{26}H_{20}Cl_2N_2O_4$: | 63.04 | 4.07 | 5.66 |
| Found: | 62.41 | 3.99 | 5.71 |

By following the procedures of Examples 7 and 8 employing the appropriate starting pentenols and acid chloride, the following compounds in Table 4 are prepared.

TABLE 4

[Structure: 6-chloro-quinoxalinyl-O-phenyl-O-CH(CH3)-CH=CH-CH2-OC(=O)-R²]

| Compound No. | R² | M.P. °C. or RI at (nD²⁵) | Molecular Formula and Elemental Analysis | | |
|---|---|---|---|---|---|
| | | | | % C | % H | % N |
| 19 | –⟨phenyl⟩–Cl (3-Cl) | 63–65 | $C_{26}H_{20}Cl_2N_2O_4$ | | | |
| | | | Calc: | 63.04 | 4.07 | 5.66 |
| | | | Found: | 62.53 | 4.07 | 5.64 |

TABLE 4-continued

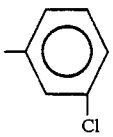

| Compound No. | R² | M.P. °C. or RI at (n_D²⁵) | Molecular Formula and Elemental Analysis | | | |
|---|---|---|---|---|---|---|
| | | | | % C | % H | % N |
| 20 | (3-chlorophenyl) | thick gum | $C_{26}H_{20}Cl_2N_2O_4$ | | | |
| | | | Calc: | 63.04 | 4.07 | 5.66 |
| | | | Found: | 62.12 | 3.90 | 5.52 |
| 21 | (3,4-dichlorophenyl) | 107-110 | $C_{26}H_{19}Cl_3N_2O_4$ | | | |
| | | | Calc: | 58.94 | 3.61 | 5.29 |
| | | | Found: | 58.83 | 3.53 | 5.11 |

EXAMPLE 12

2-(Aminocarbonyl)benzoic acid, 4-(4-((6-chloro-2-quinoxalinyl)oxy)phenoxy)-2-pentenyl ester

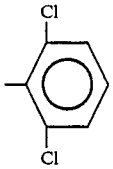

A mixture of 1.5 g (4.2 mmol) of the pentenol obtained in Example 3 above, 1.04 g (6.3 mmol) of 4-(aminocarbonyl)benzoic acid, 1.30 g (6.3 mmol) of dicyclohexylcarbodiimide (DCC), 0.05 g of 4-(dimethylamino)pyridine and 20 ml of DMF was stirred at room temperature overnight. An additional 0.3 g of DCC and 0.25 g of 4-(aminocarbonyl)benzoic acid are added and the mixture was stirred an additional 20 hours. The mixture was then poured into ether, water added and filtered. The filtrates were separated, and the organic layer washed with saturated aqueous NaHCO₃ and water, dried over MgSO₄ and evaporated to dryness. The residue was purified by preparative scale HPLC, eluting with a 3:2 hexane:acetone, mixture to give 0.55 g of the desired product as a tan, glassy solid, m.p. 144°-148° C. (Compound 22).

| Elemental Analysis: | | | |
|---|---|---|---|
| | % C | % H | % N |
| Calculated for $C_{27}H_{22}ClN_3O_5$: | 64.35 | 4.40 | 8.34 |

| Elemental Analysis: | | | |
|---|---|---|---|
| | % C | % H | % N |
| Found: | 63.97 | 4.70 | 8.06 |

EXAMPLE 13

4-(Acetylamino)benzoic acid, 4-(4-((6-chloro-2-quinoxalinyl)oxy)phenoxy)-2-pentenyl ester

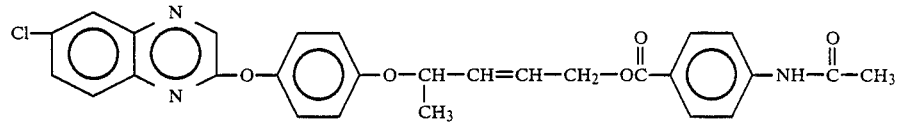

A mixture of 1.5 g (4.2 mmol) of the pentenol obtained in Example 3 above, 0.82 g (4.6 mmol) of 4-(acetylamino)benzoic acid, 0.95 g (4.6 mmol) of dicyclohexylcarbodiimide and 0.05 g of 4-(dimethylamino)-pyridine in 20 ml of dimethylformamide was stirred at room temperature for 72 hours. The mixture was diluted with ether and water and filtered. The filtrates were separated, and the organic layer washed with saturated aqueous NaHCO₃ and water, dried over MgSO₄ and evaporated to dryness. The residue was purified by preparative scale HPLC, eluting with a 65:35 hexane:acetone mixture to give 0.6 g of the desired product as a pale yellow, glassy solid, m.p. 62°-68° C. (Compound 23).

| Elemental Analysis: | | | |
|---|---|---|---|
| | % C | % H | % N |
| Calculated for $C_{28}H_{24}ClN_3O_5$: | 64.93 | 4.67 | 8.11 |
| Found: | 64.48 | 5.01 | 8.27 |

EXAMPLE 14

4-(4-((6-Chloro-2-quinoxalinyl)oxy)phenoxy)-2-penten-1-ol, methylcarbamate

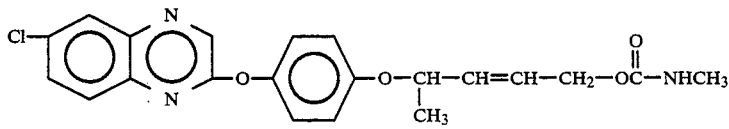

To a solution of 1.78 g (5 mmol) of the pentenol obtained in Example 3 above, and 50 ml of methylene chloride was added 3 drops of triethylamine and 0.86 g (15 mmol) of methylisocyanate. The solution was stirred at room temperature for 8 days. The solvent was separated and the residue was recrystallized twice from methylcyclohexane to give 1.68 g (81%) of the desired carbamate product as colorless crystals. The product melted at 114°–115° C. (Compound 24).

| Elemental Analysis: | | | |
|---|---|---|---|
| | % C | % H | % N |
| Calculated for $C_{21}H_{20}ClN_3O_4$: | 60.97 | 4.87 | 10.15 |
| Found: | 60.69 | 4.81 | 10.43 |

The preparation of the optical isomer forms of the active compounds follow conventional procedures employed to prepare related compounds. Such procedures include those taught in U.S. patent application No. 4,532,328; European Patent Application Nos. 2,800, 3,890 and 6,608; German OLS No. 2,949,728 and U.K. Patent Application GB No. 2,042,503A. The teachings of these applications are incorporated herein by reference thereto.

The alkenol compounds of the present invention have been found to be suitable for use in methods for the pre- and postemergent control of grassy weeds. Such weeds involved, for example, foxtail, barnyard grass, wild oats, Johnson grass and crabgrass. In addition, these compounds can be employed to control these grassy weeds in the presence of various broadleaf crop plants including sugar beets, soybeans, cotton, rape and the like.

The derivative compounds prepared from the alkenol intermediates of the present invention have been found to be suitable for use in methods for the selective postemergent control of many annual and perennial grassy weeds in the presence of corn plants.

It is to be noted that not all compounds will have the same effect on all weed plants. Some compounds will be more active in the control of one weed specie than another.

For the above herbicidal uses, unmodified active ingredients of the active compounds can be employed. However, the present invention also embraces the use of the active compounds in admixture with inert materials, known in the art as agricultural adjuvants and/or carriers, in solid or liquid form. Thus, for example, an active ingredient can be dispersed on a finely-divided solid and employed therein as a dust or granule. Also, the active ingredients, as liquid concentrates or solid compositions comprising one or more of the active ingredients can be dispersed in water, typically with aid of a wetting agent, and the resulting aqueous dispersion employed as a spray. In other procedures, the active ingredients can be employed as a constituent of organic liquid compositions, oil-in-water and water-in-oil emulsions or water dispersions, with or without the addition of wetting, dispersing, or emulsifying agents. Suitable adjuvants of the foregoing type are well known to those skilled in the art.

The herbicidally effective concentration of the active ingredients in solid or liquid compositions generally is from about 0.0003 to about 95 percent by weight or more. Concentrations from about 0.05 to about 50 percent by weight are often employed. In compositions to be employed as concentrates, the active ingredient can be present in a concentration from about 5 to about 98 weight percent. The active ingredient compositions can also contain other compatible additaments, for example, phytotoxicants, plant growth regulants and other biologically active compounds used in agriculture.

In further embodiments, the compounds of the present invention or compositions containing the same, can be advantageously employed in combination with one or more additional pesticidal compounds. Such additional pesticidal compounds may be insecticides, nematocides, miticides, arthropodicides, herbicides, fungicides or bactericides that are compatible with the compounds of the present invention in the medium selected for application and not antagonistic to the activity of the present compounds. Accordingly, in such embodiments, the pesticidal compound is employed as a supplemental toxicant for the same or for a different pesticidal use or as an additament. The compounds in combination can generally be present in a ratio of from 1 to 100 parts of the compound of the present invention with from 100 to 1 part of the additional compound(s).

The derivative compounds taught to be prepared from the alkenols of the present invention have been found to possess desirable postemergent activity against grassy weeds such as foxtail, barnyard grass, wild oats, Johnson grass and crabgrass while showing high selectivity to corn plants. These compounds are also uniquely effective in controlling perennial grassy weeds such as Johnson grass, quackgrass, and bermuda grass.

The exact amount of the active material to be applied is dependent not only on the specific active ingredient being applied, but also on the particular action desired, the weed plant species to be controlled and the stage of growth thereof as well as the part of the plant to be contacted with the toxic active ingredient. Thus, all of the active ingredients of the present invention and compositions containing the same may not be equally effective at similar concentrations or against the same weed plant species.

In the above taught pre- and postemergent operations, a dosage of about 0.01 to about 20 lbs/acre (0.056–22.4 kg/hectare) is generally applicable, although not all compounds are equally effective and some weeds are more difficult to control. Thus, a dosage rate in the range of about 0.05 to about 1.0 lb/acre (0.01–1.12 kg/hectare) is preferred in control of annual grassy weeds, while about 0.05 to about 5 lbs/acre (0.056–5.6 kg/hectare) is a preferred dosage range for the control of perennial grassy weeds.

The following examples illustrate the effects of the compounds of this invention.

EXAMPLE 15

Representative compositions of the present invention were evaluated to determine their effectiveness in preemergent operations.

Aqueous dispersions were prepared by admixing predetermined amounts of one of the hereinafter set forth compounds, dissolved in a predetermined amount of an inert solvent with a predetermined quantity of water and surfactant to dispersions of one of compound B or C as the sole toxicant.

These compositions were drenched onto the soil in plots immediately after they were seeded with predetermined plant seeds. Other plots similarly seeded with the same plant species were drenched with like compositions, containing no toxicant, to serve as controls. The plots were treated at a treating rate equivalent to 1 and 0.5 pound per acre. Thereafter, the plots were maintained under conditions conducive to good plant growth. Two weeks after treatment, the plots were examined to determine the amount of plant growth. The results of the examinations are set forth below in Table 5.

TABLE 5

| Compound Number | Treating Rate In Pounds Per Acre | Percent Kill and Control of the Following Plant Species[a] at Indicated Treating Rate | | | | | | | | | | |
|---|---|---|---|---|---|---|---|---|---|---|---|---|
| | | CT | SOY | SB | CN | RC | SG | WH | BG | CG | JG | WO | YFT |
| B | 0.5 | 0 | 0 | 0 | 0 | 10 | 100 | 10 | 60 | 100 | 100 | 50 | 95 |
| | 1.0 | 0 | 0 | 0 | 100 | 20 | 100 | 100 | 100 | 100 | 100 | 50 | 90 |
| C | 0.5 | 0 | 0 | 0 | 100 | 70 | 100 | 100 | 100 | 100 | 100 | 80 | 100 |
| | 1.0 | 0 | 0 | 0 | 100 | 100 | 100 | 100 | 100 | 100 | 100 | 100 | 100 |

[a] CT = cotton; SOY = soybean, SB = sugar beet; CN = corn; RC = rice; SG = sorghum; WH = wheat; BG = barnyard grass; CG = crabgrass; JG = Johnson grass; WO = wild oats and YFT = yellow foxtail.

EXAMPLE 16

Representative compositions of the present invention were evaluated to determine their effectiveness in postemergent operations.

Aqueous dispersions were prepared by admixing predetermined amounts of one of the hereinafter set forth compounds, dissolved in a predetermined amount of an inert solvent with a predetermined quantity of water, and a predetermined amount of a surfactant to give aqueous dispersions of compounds B, C, D, E or F as the sole toxicant.

Predetermined plant seeds were planted in beds of good agricultural soil and grown in a greenhouse. After the plants had emerged and had grown to a height of about 4 inches, the plants were sprayed to runoff with one of the above-prepared compositions at a predetermined treating rate (in parts of the active compound per million parts of the ultimate composition (PPM)). Other beds of the plants were sprayed with a water-surfactant mixture, containing no active compound, to serve as controls. After treatment, the beds were maintained for two weeks under greenhouse conditions conducive for good plant growth. At the end of this period, the beds were examined to determine the amount of kill and control. The specific plant species, test compounds and the percent postemergent control are set forth below in Table 6.

TABLE 6

| Compound Number | Treating Rate In Parts Per Million | Percent Kill and Control of the Following Plant Species[a] at Indicated Treating Rate | | | | | | | | | | | |
|---|---|---|---|---|---|---|---|---|---|---|---|---|---|
| | | CT | SOY | SB | CN | RC | SG | WH | BG | CG | JG | WO | FT |
| B | 500 | 0 | 0 | 0 | 30 | 0 | 40 | 10 | 100 | 100 | 99 | 0 | 0 |
| | 250 | 0 | 0 | 0 | 15 | 0 | 15 | 0 | 100 | 95 | 100 | 0 | 0 |
| | 125 | 0 | 0 | 0 | 0 | 0 | 10 | 0 | 100 | 100 | 100 | 0 | 0 |
| C | 250 | 0 | 0 | 0 | 100 | 90 | 90 | 100 | 100 | 100 | 100 | 70 | 100 |
| | 125 | 0 | 0 | 0 | 40 | 85 | 100 | 20 | 100 | 90 | 100 | 70 | 100 |
| | 62.5 | 0 | 0 | 0 | 20 | 80 | 100 | 20 | 100 | 95 | 100 | 20 | 100 |
| D | 500 | 0 | 0 | 0 | 100 | 98 | 90 | 100 | 100 | 100 | 100 | 98 | 100 |
| | 250 | 0 | 0 | 0 | 100 | 50 | 0 | 40 | 100 | 100 | 0 | 30 | 100 |
| | 125 | 0 | 0 | 0 | 50 | 0 | 0 | 40 | 98 | 100 | 0 | 20 | 100 |
| E | 500 | 0 | 0 | 100 | 100 | 100 | 0 | 0 | 100 | NT | 100 | 30 | 100 |
| | 250 | 0 | 0 | 100 | 100 | 98 | 0 | 0 | 100 | NT | 100 | 30 | 100 |
| F | 500 | 0 | 20 | 0 | 100 | 100 | 0 | 90 | 100 | NT | 100 | 98 | 100 |
| | 250 | 0 | 0 | 0 | 100 | 100 | 0 | 90 | 100 | 100 | 90 | 90 | 100 |

[a] CT = cotton; SOY = soybean, SB = sugar beet; CN = corn; RC = rice; SG = sorghum; WH = wheat; BG = barnyard grass; CG = crabgrass; JG = Johnson grass; WO = wild oats and FT = foxtail. NT = not tested

EXAMPLE 17

Representative compositions of the derivatives made from the alkenols of the present invention were evaluated to determine their effectiveness in postemergent operations.

Aqueous dispersions were prepared by admixing predetermined amounts of one of the hereinafter set forth compounds, dissolved in a predetermined amount of an inert solvent with a predetermined quantity of water and a predetermined amount of a surfactant to give aqueous dispersions of one of compounds 1–19 as the sole toxicant.

Predetermined plant seeds were planted in beds of good agricultural soil and grown in a greenhouse. After the plants had emerged and had grown to a height of from 2–8 inches, the plants were sprayed to runoff with one of the above-prepared compositions at a predetermined treating rate (in parts of the active compound per million parts of the ultimate composition (PPM)). Other beds of the plants were sprayed with a water-surfactant mixture, containing no active compound, to serve as controls. After treatment, the beds were maintained for two weeks under greenhouse conditions conducive for good plant growth. At the end of this period, the beds were examined to determine the amount of kill and control. The specific plant species, test compounds and the percent postemergent control are set forth below in Table 7.

TABLE 7

| Compound No. Tested | Treatment Rate in PPM | Percent Kill and Control of the Following Plant Species | | | |
|---|---|---|---|---|---|
| | | Corn | Crab-grass | Johnson Grass | Giant Foxtail | Green Foxtail |
| 1 | 1000 | 0 | NT | 90 | 85 | 90 |
| | 500 | 0 | NT | 75 | 85 | 80 |
| 2 | 500 | 0 | 100 | NT | 100 | 100 |
| | 250 | 0 | 100 | NT | 100 | 100 |
| 3 | 250 | 0 | NT | 100 | 100 | 100 |
| | 125 | 0 | NT | 100 | 100 | 100 |
| 4 | 500 | 0 | 80 | NT | 98 | 98 |
| | 250 | 0 | 80 | NT | 100 | 98 |
| 5 | 500 | 0 | 100 | NT | 100 | 100 |
| | 250 | 0 | 100 | NT | 100 | 100 |
| 6 | 500 | 0 | 98 | NT | 100 | 100 |
| | 250 | 0 | 70 | NT | 98 | 100 |
| 7 | 500 | 0 | 95 | NT | 100 | 98 |
| | 250 | 0 | 90 | NT | 100 | 98 |
| 8 | 500 | 0 | 100 | NT | 100 | 100 |
| | 250 | 0 | 100 | NT | 100 | 100 |
| 9 | 500 | 10 | NT | 100 | 100 | 100 |
| | 250 | 0 | NT | 100 | 100 | 100 |
| 10 | 500 | 20 | NT | 100 | 100 | 100 |
| | 250 | 0 | NT | 100 | 100 | 100 |
| 11 | 62 | 10 | NT | 100 | 100 | 100 |
| | 31 | 0 | NT | 80 | 90 | 20 |
| 12 | 125 | 20 | NT | 100 | 100 | 100 |
| | 62 | 0 | NT | 100 | 100 | 100 |
| 13 | 500 | 10 | NT | 100 | 100 | 100 |
| | 250 | 0 | NT | 100 | 100 | 100 |
| 14 | 250 | 20 | NT | 100 | 100 | 100 |
| | 125 | 0 | NT | 100 | 90 | 50 |
| 15 | 500 | 20 | NT | 100 | 100 | 100 |
| | 250 | 0 | NT | 100 | 100 | 100 |
| 16 | 250 | 20 | NT | 100 | 100 | 100 |
| | 125 | 0 | NT | 100 | 90 | 95 |
| 17 | 250 | 0 | NT | NT | 94 | NT |
| | 125 | 0 | NT | NT | 92 | NT |
| 18 | 250 | 5 | NT | NT | 90 | NT |
| | 125 | 5 | NT | NT | 90 | NT |
| 19 | 250 | 5 | NT | NT | 98 | NT |
| | 125 | 0 | NT | NT | 98 | NT |

What is claimed is:

1. A compound or an optical isomer thereof corresponding to the formula wherein
Y and $Y^1$ each independently represent —H or —F;
P represents methyl or ethyl;
T represents ${+CH_2—CH_2)_a(CH=CH)_b}$ and the cis (Z) or trans (E) stereoisomers thereof or ${+CH_2—CH_2)_a(C≡C)}$;
A represents =N;
a represents the integer 0, 1 or 2;
b represents the integer 1 or 2; and
X represents —Br, —Cl, —F or —CF$_3$.

2. A compound as defined in claim 1 which is in the R enantiomeric isomer form.

3. A compound as defined in claim 1 which is in the E stereoisomer form.

4. A compound as defined in claim 1 wherein X is —Br, —Cl or —F, a is 0, b is 1 and P is methyl.

5. A compound as defined in claim 4 wherein X is —Cl.

6. The compound as defined in claim 5 which is 4-(4-((6-chloro-2-quinoxalinyl)oxy)phenoxy)-2-penten-1-ol.

7. The compound as defined in claim 6 which is in the E stereoisomer form.

8. A compound as defined in claim 4 wherein X is —F.

9. The compound as defined in claim 8 which is 4-(4-((6-fluoro-2-quinoxalinyl)oxy)phenoxy)-2-penten-1-ol.

10. A compound as defined in claim 4 wherein X is —Br.

11. The compound as defined in claim 10 which is 4-(4-((6-bromo-2-quinoxalinyl)oxy)phenoxy)-2-penten-1-ol.

12. A composition which comprises an agriculturally acceptable inert adjuvant in intimate admixture with a herbicidally effective amount of a compound or an optical isomer thereof, as the active material, which corresponds to the formula wherein
Y and $Y^1$ each independently represent —H or —F;
P represents methyl or ethyl;
T represents ${+CH_2—CH_2)_a(CH=CH)_b}$ and the cis (Z) or trans (E) stereoisomers thereof of ${+CH_2—CH_2)_a(C≡C)}$;
A represents =N;
a represents the integer 0, 1 or 2;
b represents the integer 1 or 2; and
X represents —Br, —Cl, —F or —CF$_3$.

13. A composition as defined in claim 12 wherein the compound is in the R enantiomeric isomer form.

14. A composition as defined in claim 12 wherein the compound is in the E stereoisomer form.

15. A composition as defined in claim 12 wherein X is —Br, —or —F, a is 0, b is 1 and P is methyl.

16. A composition as defined in claim 15 wherein X is —Cl.

17. The composition as defined in claim 16 wherein the compound is 4-(4-((6-chloro-2-quinoxalinyl)-oxy)-phenoxy)-2-penten-1-ol.

18. The composition as defined in claim 17 wherein the compound is in the E stereoisomer form.

19. A composition as defined in claim 15 wherein X is —F.

20. The composition as defined in claim 19 wherein the compound is 4-(4-((6-fluoro-2-quinoxalinyl)-oxy)-phenoxy)-2-penten-1-ol.

21. A composition as defined in claim 15 wherein X is —Br.

22. The composition as defined in claim 21 wherein the compound is 4-(4-((6-bromo-2-quinoxalinyl)-oxy)-phenoxy)-2-penten-1-ol.

23. A method for the postemergent kill and control of grassy weeds which comprises applying to said weeds a herbicidally effective amount of a composition comprising an agriculturally acceptable inert adjuvant in intimate admixture with, as the active material, a compound or an optical isomer thereof, as the active material, which corresponds to the formula

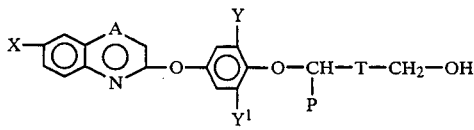

wherein
Y and $Y^1$ each independently represent —H or —F;
P represents methyl or ethyl;
T represents $-(CH_2-C_2)_a(CH=CH)_b$ and the cis (Z) or trans (E) stereoisomers thereof or $-(CH_2-CH_2)_a(CH\equiv C)$;
A represents $\equiv N$;
a represents the integer 0, 1 or 2;
b represents the integer 1 or 2; and
X represents —Br, —Cl, —F or —CF$_3$.

24. A method as defined in claim 23 wherein the compound is in the R enantiomeric isomer form.

25. A method as defined in claim 23 wherein the compound is in the E stereoisomer form.

26. A method as defined in claim 23 wherein X is —Br, —Cl or —F, a is 0, b is 1 and P is methyl.

27. A method as defined in claim 26 wherein X is —Cl.

28. The method as defined in claim 27 wherein the compound is 4-(4-((6-chloro-2-quinoxalinyl)oxy)-phenoxy)-2-penten-1-ol.

29. The method as defined in claim 28 wherein the compound is in the E stereoisomer form.

30. A method as defined in claim 26 wherein X is —F.

31. The method as defined in claim 26 wherein the compound is 4-(4-((6-fluoro-2-quinoxalinyl)oxy)-phenoxy)-2-penten-1-ol.

32. A method as defined in claim 26 wherein X is —Br.

33. The method as defined in claim 32 wherein the compound is 4-(4-((6-bromo-2-quinoxalinyl)oxy)-phenoxy)-2-penten-1-ol.

* * * * *